US00PP22092P3

(12) United States Plant Patent
Korlipara

(10) Patent No.: US PP22,092 P3
(45) Date of Patent: Aug. 23, 2011

(54) ***AJUGA* PLANT NAMED 'BLUEBERRY MUFFIN'**

(50) Latin Name: *Ajuga reptans*
Varietal Denomination: Blueberry Muffin

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 22 days.

(21) Appl. No.: 12/653,631

(22) Filed: Dec. 14, 2009

(65) Prior Publication Data

US 2011/0145960 P1 Jun. 16, 2011

(51) Int. Cl.
*A01H 5/00* (2006.01)

(52) U.S. Cl. ..... Plt./401

(58) Field of Classification Search ..... Plt./401
See application file for complete search history.

*Primary Examiner* — Kent L Bell
(74) *Attorney, Agent, or Firm* — Klarquist Sparkman, LLP

(57) ABSTRACT

A new and distinct cultivar of *Ajuga reptans* characterized by its combination of outstanding vigor, small chocolate brown narrow leaves, and a mounding, creeping habit.

1 Drawing Sheet

Botanical denomination: *Ajuga reptans.*
Variety designation: 'Blueberry Muffin'.

BACKGROUND OF THE INVENTION

The present invention relates to a new and distinct cultivar of *Ajuga reptans,* given the name, 'Blueberry Muffin'. *Ajuga* is in the family Lamiaceae. This plant originated from a naturally occurring meristematic mutation of *Ajuga* 'Chocolate Chip' (an unpatented plant with the synonym 'Valfredda'). The mutated plant was found in a garden at an Oregon nursery.

*Ajuga* 'Blueberry Muffin' is unique in its combination of vigor, small chocolate brown narrow leaves, and mounding, creeping habit.

Compared to *Ajuga* 'Chocolate Chip', the new cultivar is more vigorous. It fills a 1 gallon pot quickly and has a mounding instead of a creeping habit when young. In its first spring in the ground from a one gallon it has spread to 40 cm wide in Canby, Oregon. *Ajuga* 'Blueberry Muffin' has leaves that are broader near the tip and shorter than *Ajuga* 'Chocolate Chip'.

The new variety has been reproduced only by asexual propagation (division, cuttings, and micropropagation from apical buds). Each of the progeny exhibits identical characteristics to the original plant. Asexual propagation by division, cuttings and micropropagation by apical buds as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a one-year-old *Ajuga* 'Blueberry Muffin' growing in the garden in late spring in Canby, Oregon.

FIG. 2 shows a two year old plant in a one gallon pot growing in a cold greenhouse in mid winter.

FIG. 3 shows a summer planting in the garden with flowers.

DETAILED PLANT DESCRIPTION

The following is a detailed description of the new *Ajuga* cultivar based on observations in April of two-year-old specimens grown outside in the ground in the garden in Canby, Oreg. The color descriptions are all based on The Royal Horticultural Society Colour Chart, 5$^{th}$ edition.

Plant

*Form.*—Stoloniferous, herbaceous perennial.
*Cold hardiness.*—USDA Zone 6-9.
*Size.*—Grows to 45 cm wide and 7 cm high.
*Vigor.*—Excellent.
*Stem.*—Rosette from short, thick stem, grows to 20 mm long and 4 mm wide, internodes 2 mm long, Greyed Purple 186C.
*Roots.*—Grey Brown 199D, thickened to fibrous, plants root easily from divisions.
*Stolons.*—Grey Brown 199D, grows to 20 cm long and 2 to 3 mm wide, internodes grow to 30 mm long.
*Finish time.*—The new cultivar finishes to a 4" pot in 4 to 6 weeks from a 72 cell plug.

Leaf:

*Type.*—Simple.
*Arrangement.*—Opposite in a basal rosette.
*Number of leaves per stem.*—About 20.
*Shape.*—Spatulate.
*Venation.*—Pinnate. Main vein color on top and bottom side Green 147A.
*Margins.*—Entire.
*Apex.*—Obtuse.
*Base.*—Attenuate.
*Blade size.*—Grows to 5 cm long and 1.4 cm wide.
*Surface texture.*—Very sparsely pubescent on both sides.
*Petiole description.*—Grows to 4 cm long and 3 mm wide, very sparsely pubescent, Yellow Green 146D.
*Leaf color.*—Topside spring and older leaves summer: Green 137A. Topside summer, younger leaves: Brown 200B. Topside fall, winter leaves: closest to Greyed Purple N186A. Bottom side: Green 147A.

Inflorescence:

*Type.*—Terminal spike.

*Number of flowers.*—70 per spike in two to five flowered, dense whorls.

*Peduncle.*—12 cm tall and 3 mm wide, sparsely pubescent, Grey Purple 187B in the sun and Yellow Green 146B in the shade.

*Pedicel.*—Sessile to 2 mm long and 0.7 mm wide, pubescent, Greyed Purple N186C.

*Bracts.*—Subtending flowers, 12 to 16 in number, opposite, sessile, tip obtuse, margin entire, ovate to broadly elliptic, size changes from bottom leaf 0.5 cm wide and 1.5 cm long to top 27 mm long and 18 mm wide, topside Green 137A on shade leaves and Greyed Purple 186NB on sun leaves, bottom side Green 137A.

*Bloom period.*—April to June in Canby, Oreg.

Flower bud:

*Size.*—7 mm long and 3 mm wide at the widest point prior to opening.

*Description.*—Tubular.

*Surface texture.*—Villous.

*Color.*—Closest to Violet Blue 97A.

Flower:

*Type.*—Zygomorphic.

*Shape.*—Bilabiate.

*Corolla description.*—1.5 cm long and spreads to 9 mm wide, tube and throat 9 mm long and 2 mm to 3 mm wide; 2 small upper lobes each 1.5 mm long and 1.5 mm wide, acute, three lower lobes, two spreading sideways each 3 mm long and 1.5 mm wide, tip notched to obtuse to mucronulate; the terminal lobe two lobed 5 mm long and obovate in shape, margin entire, tips obtuse, glabrous inside, villous outside, color inside Violet Blue N89B, outside Violet Blue 94B.

*Calyx description.*—5 lobed, 3 mm long and 3 mm wide, acute, entire, pubescent outside, glabrous inside, Greyed Purple N186C inside and outside.

*Pistil description.*—One, 11 mm long, ovary 0.5 mm long, Yellow Green 145A, style and stigma 10.5 mm long, Violet Blue N89B at the tip to N88B at the base.

*Stamen description.*—Four, 3 mm long, Violet Blue N89D, anthers 0.5 mm long, Greyed Purple N189A.

*Pollen.*—Yellow 8A in color.

*Fragrance.*—None.

*Lastingness.*—A spike blooms for about 3 weeks on the plant.

*Fruit.*—None, plant sterile.

*Seed.*—None, plant sterile.

*Pests and diseases.*—*Ajuga* are known to be susceptible to southern blight and various fungal leaf spots, crown rot, and fungal root rot. The new cultivar has shown good mildew resistance in Canby, Oreg.

I claim:

1. A new and distinct cultivar of *Ajuga* plant substantially as shown and described.

* * * * *

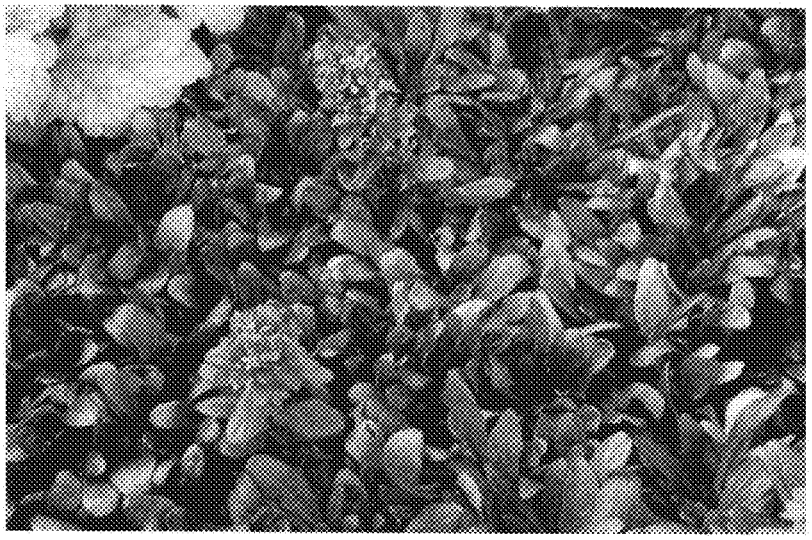

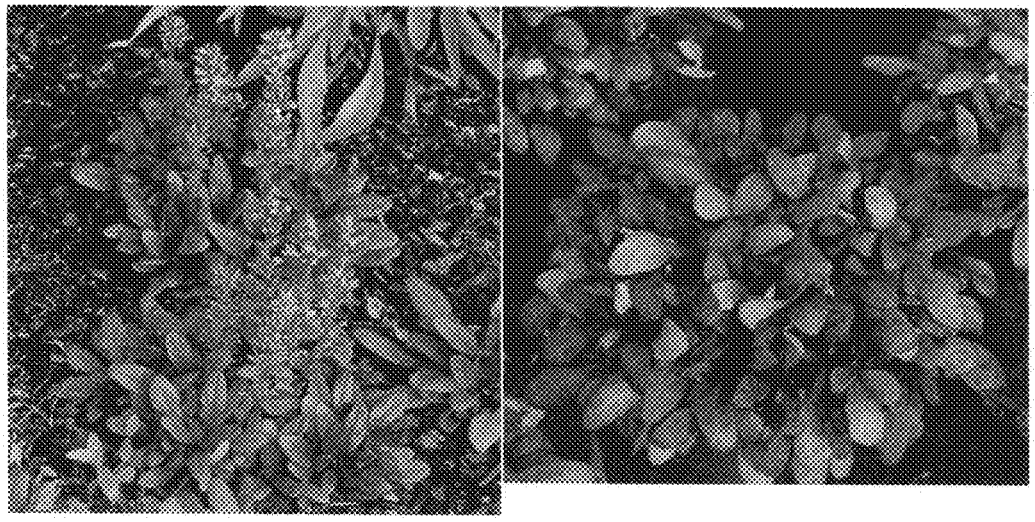
Figure 1 above left, Figure 2 above right, Figure 3 below.